(12) United States Patent
Ivins et al.

(10) Patent No.: US 6,387,665 B1
(45) Date of Patent: May 14, 2002

(54) METHOD OF MAKING A VACCINE FOR ANTHRAX

(75) Inventors: Bruce Ivins, Frederick; Patricia Worsham, Jefferson; Arthur M. Friedlander, Gaithersburg; Joseph W. Farchaus; Susan L. Welkos, both of Frederick, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/520,215

(22) Filed: Mar. 7, 2000

Related U.S. Application Data

(62) Division of application No. 08/346,238, filed on Nov. 23, 1994.

(51) Int. Cl.$^7$ ................................................. C12P 21/04
(52) U.S. Cl. .................... 435/71.1; 435/69.1; 435/69.4; 435/320.1; 435/172.1; 435/172.3; 435/252.3; 435/200.1; 435/252.31; 530/350; 424/184.1; 424/234.1; 424/246.1
(58) Field of Search ........................ 424/184.1, 234.1, 424/246.1; 530/350; 435/69.1, 69, 71.1, 320.1, 172.1, 172.3, 252.3, 252.31, 200.1

(56) References Cited

U.S. PATENT DOCUMENTS

| | | | |
|---|---|---|---|
| 3,208,909 A | 9/1965 | Puziss et al. | |
| 4,455,142 A | 6/1984 | Martins et al. | |
| 5,071,748 A | 12/1991 | Miller | |
| 5,077,214 A | 12/1991 | Guarino et al. | |
| 5,081,029 A | 1/1992 | Zarling et al. | |

OTHER PUBLICATIONS

Ivins et al. European J. Epidemiology. Mar. 1988. 4(1): 12–19*

Ivins et al. Clin. Immunology Newsletter. 9(2): 30–32, 1988.*

Uptake of Congo red by Virulent Strains of Bacillus Anthracis, Worsham et al., 1991 ASM Abstracts, p. 75.

Understanding Biotechnology Law, edited by Gale R. Peterson, Marcel Dekker, Inc., (date unknown).

Vaccine Efficacy of Bacillus anthracis Protective Antigen Produced in Pokaryotic and Eukaryotic Cells, Ivins, et al., Inst. Infect. Dis., Ft. Detric Frederick, MD, May 25, 1994.

Immunization Against Anthrax with Aromatic Compound Dependent (Aro–) Mutants of Bacillus anthracis and with Recombinant Strains of Bacillus subtilis that Produce Anthrax Protective Antigen; Ivins, et al., Infect. and Immunity, Nov. 1986, vol. 54, No. 2, pp. 537–542.

Cloning and Expression of teh Bacillus anthracis, Ivins, et al.; Infect and Immunity, May 1986, vol. 52, No. 2, pp. 454–458.

Expression of the Bacillus antracis Protective Antigen Gene by Baculovirus and Vaccinia Virus Recombinants; Icono–Connors, et al., Infect. and Immunity, Feb. 1990, vol. 58, No. 2, pp. 366–372.

Protection against Anthrax with Recombinant Virus–Expressed Protective Antigen in Experimental Animals; Iacono–Connors, et al., Infect. and Immunity, Jun. 1991, vol. 59, No. 6, pp. 1961–1965.

* cited by examiner

*Primary Examiner*—Jennifer E. Graser
(74) *Attorney, Agent, or Firm*—Elizabeth Arwine; John Francis Moran; Charles H. Harris

(57) ABSTRACT

A method of making a vaccine for anthracis that inolves a bacterial expression system and production and use of protective antigen (PA) against *Bacillus anthracis*. The PA immunogen is useful in a vaccine against human anthrax. The PA can be produced by an asporogenic organism which produces the desired antigen, which is then harvested from the supernatant.

5 Claims, No Drawings

METHOD OF MAKING A VACCINE FOR ANTHRAX

This application is a divisional application of Ser. No. 08/346,238 filed Nov. 23, 1994, said application allowed.

FIELD OF THE INVENTION

This invention relates to the bacterial expression system, production and use of protective antigen (PA) against *Bacillus anthracis*. The PA immunogen is useful in vaccine against human anthrax. The PA can be produced by an asporogenic organism which overproduces the desired antigen, which is then harvested from the supernatant.

BACKGROUND OF THE INVENTION

*Bacillus anthracis* is the etiologic agent responsible for anthrax, a disease often found in persons exposed to infected animals or their products. Persons particularly exposed to animals include veterinarians, laboratory technicians, ranchers and employees working with skin or hair of animals. The mode of entry into the body may be the skin or, when contaminated meat is eaten, the gastrointestinal tract. Inhaling of spores can cause inhalation anthrax, a disease that can be fatal. Vaccines against *Bacillus anthracis* have been available. Virulent strains of the organism produce two toxins and a poly-D-glutamic acid capsule which are coded for on two endogenous plasmids, pX01 and pX02, respectively. Loss of either of the plasmids results in an attenuated strain of reduced virulence, while loss of both results in an avirulent organism. The history of the USAMRIID Sterne strain of *B. anthracis* prior to 1981 is uncertain, though it is believed to be derived from the Sterne strain isolated at the Onderstpoort Research Laboratory in Pretoria, South Africa.

In 1985 the *Bacillus anthracis* protective antigen (PA) gene was cloned into a plasmid (pUB110) resulting in the formation of a recombinant plasmid identified as pPA102, which was reported in the literature (Ivins and Welkos, *Infection and Immunity*, 54:537–542 (1986)). The production of vaccines lacking lethal factor was possible thereby. However, a primary problem remained, since the *Bacillus anthracis* formed spores. Once spores have formed, they persist in the environment for months and years. Once the laboratory environment contains such spores, it is very difficult to free the environment of the spores.

It was also previously reported that protective antigen (PA) could be produced in baculovirus. [Iacono-Connors, et al., *Infection and Immunity*, 58:366–372 (1990); Iacono-Connors, et al., *Infection and Immunity*, 59:1961–1965 (1991)] A major problem in production of the PA in the baculovirus disclosed therein is that the desired antigen requires a complex purification process. Even after purification by immuno-affinity chromatography, undesired cellular material continues to contaminate the desired product.

DETAILED DESCRIPTION OF THE INVENTION

The instant invention provides organisms which produce protective antigen (PA) lacking lethal factor and edema factor proteins which, when present as contaminants in vaccine, can cause serious side effects. The producing organisms of the invention are also, surprisingly, non-sporulating. Furthermore, the desired antigen is expressed into the supernatant. Hence, the protective antigen produced is easily purified and, though protective, does not cause many of the troublesome side effects of prior art vaccines. The organisms of the invention lacking spore-forming function may be killed by heat shock at temperatures as low as 60° C. for 60 minutes. Hence, contamination of the environment with viable spore-forming organisms is easily avoided and decontamination is easily accomplished.

Genesis of ΔSterne-1(pPA102)CR4:

A 6 kb Bam HI fragment harboring the PA structural gene isolated from the endogenous Sterne plasmid pXO1 was ligated into plasmid pBR322 and cloned into *Escherichia coli* bacteria (Vodkin and Leppla, 1983). From the resultant recombinant plasmid pSE36, the 6 kb fragment was then subcloned into the gram-positive vector pUB110 using the Bam HI restriction site. The resulting plasmid was transformed into *B. subtilis* IS53 and two stable PA producing, kanamycin resistant isolates were found (pPA101 and pPA102) (Ivins and Welkos, 1986). Subsequent analysis of the plasmids revealed that both had suffered spontaneous deletions. The pPA102 was found to have lost 4.2 kb of DNA from 363 bp 3' of the kanamycin resistance gene to approximately 164 bp 5' of the start of the PA structural gene, a result consistent with the observed inactivation of the phleomycin resistance gene of pUB110. The plasmid was then electrotransformed into ΔSterne-1, a plasmid-free strain of *B. anthracis* (Infection and Immunity, 52:454–458 (1986) and transformants were selected for kanamycin resistance. Transformants displaying a stable PA+, kanamycin resistant, (LF-, EF-, capsule-) phenotype were selected. This strain, ΔSterne-1(pPA102), was then subjected to Congo Red agar selection for mutants displaying an inability to bind the dye, a characteristic known to correlate with an asporogenic phenotype (Worsham, submitted). The selected isolate, now designated ΔSterne-1(pPA102)CR4 was further subcultured three times to insure that a single clone was isolated. This clone has served as the seed stock for all research and development of fermentation conditions, and purification of PA.

Materials and Methods:

Fermentation Conditions

Media: FA medium was used for all plates and liquid cultures described here unless otherwise specified. FA medium consisted of 33 g/l tryptone (Difco), 20 g/l yeast extract (Difco), 2 g/l L-histidine, 8 g/l Na2HPO4, 7.4 g/l NaCl, 4 g/l KH2PO4 adjusted to pH 7.4 with NaOH.

Precultures: A working stock of ΔSterne-1(pPA102)CR4 was prepared from the seed culture by streaking cells on an FA medium plate containing 40 μg/ml of kanamycin. A sweep from the confluent growth zone on plate was cultured one time in liquid FA medium supplemented with kanamycin 40 μg/ml to a final $O.D._{600nm}$ of 4.0. This culture was checked for purity by streaking on SBA plates, and diluted into multiple vials containing sterile 100% glycerol to a final glycerol concentration of 50% (v/v). These stocks were stored at −70° C. A single vial was removed at the start of each fermentation cycle and discarded after use. The defrosted cells were streaked onto FA plates containing 40 μg/ml kanamycin and incubated at least 16 hrs at 37° C. After 16 hrs the plated cells were used to inoculate 50 mls of FA medium supplemented with 40 μg/ml kanamycin in a 250 ml baffled-Erlenmeyer flask (Bellco Laboratories). The culture was incubated at 37° C. at 200 rpm for 6 hrs or until an $O.D._{600nm}$ of 4–6 was obtained. The cells were then subcultured into 50 mls of FA medium in an identical flask under identical conditions. After 6 hrs, or a culture $O.D._{600nm}$ of 6.2–6.5, a 1.6% (v/v) inoculum was transferred to 300 mls of PA medium supplemented with 40 μg/ml kanamycin in a 2 liter baffled Erlenmeyer and incubated at 37° C. at 200 rpm for 7 hrs, or until a final O.D.$_{600nm}$ of 3.5–3.7 was achieved.

Fermentation conditions: The fermentations described here were carried out using a New Brunswick Bio-Flo 3000 equipped with a 5.0 liter working volume glass vessel and stainless steel headplate and hemispherical bottom cooling dish. Four liters of FA medium were added to the vessel, which had been previously completely disassembled, scrubbed in a dilute Envirochem solution and autoclaved for 15 min after the addition of 4 liters of H2O. The polarographic $DO_2$ probe (Ingold) and pH probes (either liquid or gel filled, Ingold) were also inserted and all addition and sampling ports were sealed or clamped and wrapped in aluminum foil. Addition lines consisted of surgical grade autoclavable Tygon tubing (Thomas Scientific) and all lines were sealed with the exception of the condenser, which was left open to permit pressure release, but covered with aluminum foil. The vessel was autoclaved using a 10 min exposure time at 121° C. and removed from the autoclave as soon as sufficient cooling had occurred to allow opening of the autoclave. The vessel was then immediately connected to the fermentor unit and the condenser line was connected to a sterile liquid trap and 0.2$\mu$ capsule filter to avoid the introduction of contaminants during the cooling process. The vessel was then cooled to 37° C. using the fermentor driven temperature control and positive pressure was provided using compressed sterile filtered air. Once the vessel had cooled to 37° C. sterile filtered kanamycin was added to a final concentration of 40 $\mu$g/ml. The agitation was activated at 150 rpm and aeration was adjusted to 1–1.2 volume/volume/min (vvm) and antifoam C (DOW), that had been diluted 10-fold into $H_2O$ and autoclaved, was added to a final concentration of 200 ppm.

A preinoculation sterility check was conducted for a minimum of 16 hrs during which time pH, agitation and temperature were continually monitored. After the 16 hrs required for $DO_2$ probe polarization, the $DO_2$ was also monitored along with turbidity. The $D_2$ probe was calibrated using an INGOLD calibration device which sets the zero value to 4 mA and 100% to the oxygen tension determined by the solubility of oxygen in the medium after aeration and agitation at 37° C. The calibration and response of the electrode was then checked by sparging with pure $N_2$. The vessel was judged to be sterile if the pH and $DO_2$ remained constant and no increase in turbidity was observed. It should be emphasized that the short autoclave cycle for vessel sterilization was required to minimize caramelization, Millard and other chemical degradation reactions which are problematic due to the high concentrations of yeast extract and tryptone in FA medium. As an additional confirmation of sterility, 50 mls was aseptically removed from the fermentor to a 250 mls Erlenmeyer and incubated at 37° C. at 200 rpm for 48 hrs with no sign of growth. Under the conditions outlined here contamination has not been observed in more than 10 fermentation cycles.

Once the sterility of the vessel had been verified, the 300 ml inoculum described above was added to the vessel through the addition port of the headplate and the initial O.D.$_{600nm}$ was recorded. A sample of the inoculum was also streaked on SBA plates and incubated for 48 hrs at 37° C. to verify inoculum purity. Using the Bio-Flo 3000, aeration was maintained at 75% of saturation by increasing agitation from the initial 150 rpm to a maximum of 400 rpm and ultimately by supplementing the 1 vvm aeration rate with pure oxygen. The mixture rate and percentages of air and oxygen were controlled by a solenoid and algorithm developed by Nev Brunswick Scientific. Both gases had a working pressure of approximately 10 psi.

The O.D.$_{600nm}$ dry cell weight (DCW), production of PA, $DO_2$, pH, agitation and temperature were monitored throughout each fermentation cycle. The O.D.$_{600nm}$ DCW and PA production analysis were carried out by manually sampling the fermentation liquor at hourly intervals using a sterile sampling port. O.D.$_{600nm}$ was measured after dilution of the culture using sterile medium prepared for that fermentation. For each O.D.600 determination, two appropriate dilutions were made and results were considered acceptable only when both dilutions yielded a linear response. DCWs were determined starting with a 2 hr point by centrifuging 10 mls of fermentation liquor at 11,953×g for 10 min, resuspending the cell pellet in 10 mls of sterile PBS and pelleting the cells again under the same conditions. The cell pellet was resuspended in a minimal volume of PBS and transferred quantitatively to a preweighted Eppendorf centrifuge tube and centrifuged at 14,000 rpm for 5 min. Excess PBS was removed and the cell pellet was dried in a speed-vac for 72 hrs under vacuum and a medium heat setting. A final analysis of the dry weight versus O.D.$_{600nm}$ revealed that the relationship between the two parameters was adequately fit with a linear function.

Fermentation Reproducibility: The reproducibility of the cell growth parameters, biomass and PA production in fermentations carried out with the Bio-Flo 3000 under the conditions described above have been summarized in Table I below. Two fermentations were carried out at 75% of the maximum dissolved oxygen concentration in a strict batch mode with no pH control or additions other than antifoam C. The variation in the agitation rate during the first 100 min of the fermentation was the result of the $AGDO_2$ (agitation $DO_2$) control mode chosen to maintain the dissolved oxygen tension at 75% of the maximum. Briefly, this algorithm attempts to control the oxygen tension by first altering the agitation rate until this proves insufficient, at which point the process air is supplemented with pure oxygen as needed to maintain the desired $DO_2$. The temperature was held constant at 37°+/− 0.1° C. The pH was monitored, but not regulated as an internal check on the aeration of the vessel during the course of the fermentation. The fact that the pH revealed a decrease on only 0.2 pH units in the first 150 min was consistent with an aerobic culture metabolizing the limited carbohydrate supplied with the yeast extract to $CO_2$ and organic acids. Once the carbohydrate was exhausted after ca. 150 min, the bacillus switched to the utilization of amino acids and peptides for a carbon source, which under aerobic conditions resulted in the release of $NH_4OH$ and the observed increased culture pH.

These fermentations were sampled on an hourly basis and allowed to proceed until no further increase in O.D.$_{600nm}$ was observed over two time points. O.D.$_{600nm}$, DCW analysis and product measurements were carried out for each sample as described above. Samples for PA production were sterile filtered followed by the addition of HEPES and the complete protease cocktail as described under PA quantitation. The samples were concentrated, desalted and ultimately concentrated 80-fold prior to being analyzed using SDS-PAGE. The major band of the gel corresponded to the 83 kDa PA product. An increasing in the intensity of the protein band was seen with increasing fermentation time. Study of a Western blot of another time course of a batch fermentation was developed with polyclonal rabbit anti-PA83. Comparison revealed that along with increasing PA 83 kDa there was also a pronounced increase in the abundance and form of proteolytic degradation products of PA.

TABLE 1

Summary of Aerobic ΔSterne-1(pPA102)CR4 Fermentations

| Fermentation Conditions | Final Conc. (μg PA83/ml | Final Yield (mg PA83) | Final Yield (mg PA83/g DCW) | Specific Growth Rate | Doubling Time $T_D$ (min) |
|---|---|---|---|---|---|
| Aerobic, Batch | 51 | 235 | 8.10 | 0.0132 $min^{-1}$ | 53 |
| Aerobic, Batch | 64 | 301 | 10.7 | 0.0136 $min^{-1}$ | 51 |
| Aerobic, Batch pH constant | 45 | 225 | 7.40 | 0.0136 $min^{-1}$ | 51 |
| Aerobic, Fed-Batch (non-continuous) | 68 | 360 | ND | 0.0116 $min^{-1}$ | 60 |

DCW = dry cell weight

The data presented in Table 1 demonstrated that the PA yield on a unit volume and biomass basis, as well as the cell growth parameters, were reproducible for the batch fermentations conducted without pH control. The final fermentation pH values of 8.57 and 8.67 after an elapsed fermentation time of ca. 8 hrs were also comparable. The effect of prolonged exposure to these mildly alkaline conditions on cell growth, PA production and subsequent degradation was investigated by repeating the fermentation at a constant pH of 7.50+/−0.05 pH units. This was accomplished using the immersed vessel pH probe and automated additions of 2 N HCl or 1 N NaOH. The results shown in Table 1 demonstrate that there was no clear effect of constant pH on any of the parameters evaluated. SDS-PAGE analysis of the fermentation time points sampled for PA production also revealed no significant differences.

The final fermentation presented in Table 1 was a non-continuous fed-batch trial during which 1/10 volume of a 10-fold concentrate of sterile-filtered tryptone was added after 5 hrs or an $O.D._{600nm}$ of 7.5. The result suggested that such fed-batch fermentations provide possible protocols for improvement to increase yield and decrease proteolysis.

Harvest conditions: Fermentations were allowed to proceed until no further increase in $O.D._{600nm}$ was observed. At this point, the fermentor was cooled to 10° C. and the protease inhibitors phenylmethylsulfonyl fluoride (PMSF), 1,10-phenanthroline (OP) and ethylenediamine tetraacetate (EDTA) were added to final concentrations of 0.1, 0.05 and 2 mM, respectively. The cells were then pumped from the fermentor vessel at room temperature using an Amicon DC10L concentrator equipped with a 10-$ft^2$ 0.1 μpolysulfone hollow-fiber cartridge. The fermentor liquor was diluted 1:1 with 25 mM diethanolamine (DEA), 50 mM NaCl, 2 mM EDTA, 0.1 mM PMSF adjusted to pH 8.9 with HCl. The filtrate was collected at an operating pressure of less than 20 psi and transferred directly to a second Amicon DC10L equipped with two 30 kDa cutoff 10-$ft^2$ wound spiral cellulosic cartridges. The filtrate was concentrated approximately 10-fold before being subjected to diafiltration at an operating pressure of less than 30 psi against the same buffer. The conductivity of the retentate was monitored with an Amber Sciences conductivity meter and platinum immersion pencil-type electrode. The diafiltration step generally required 20 liters of buffer, but was considered complete only after the conductivity of the concentrated retentate was equivalent to that of the starting buffer.

Quantitation of 83 kDa PA in crude fermentation liquor: The fermentation liquor was sampled using a sterile port at regular intervals throughout the fermentation process. The samples for PA determination were filtered through syringe type 0.2μ cellulose acetate filters, 0.1 mM PMSF, 2 mM EDTA, 50 μM OP and 20 mM HEPES pH7.3 were added and the samples were frozen at −70° C. The samples were defrosted on ice and concentrated using Amicon Centricon 30 concentrators at 4500×g. The samples were concentrated approximately 10-fold, diluted to the original volume with 10 mM TRIS pH8.0, 0.1 mM PMSF, 2 mM EDTA, 0.05 pM OP and concentrated again. The concentrated sample was desalted again using the same buffer, frozen and finally lyophilized using a Speed-Vac. The dried samples were dissolved in 25 μl of the TRIS buffer described above and diluted 1:1 with a 2×SDS solubilization buffer consisting of 50 mM $Na_2CO_3$, 4% (w/v) SDS, 12% (v/v) glycerol, 2% (v/v) 2-mercaptoethanol and 0.01% (w/v) Bromphenol Blue prior to heating at 95° C. for 5 min. The fermentation samples containing varying amounts of PA 83 kDa were solubilized as described above and run on a Daiichi 4–20% gradient TRIS/TRICINE gel to approximate total yield of PA. Two hundred to 2000 ng samples of purified PA were solubilized in the same buffer and loaded onto the gel in constant total volume of 3 μl. Three or four appropriate dilutions of the fermentation samples determined from the first gel were loaded onto the gel with the standards and electrophoresed at 100 V initially and 140 V once the samples entered the separating gel and until the Bromphenol Blue dye reached the bottom edge of the separating gel. The gel was then fixed in 10% (v/v) acetic acid 20% (v/v) MeOH for 10 min, rinsed with MQ $H_2O$ and stained with Coomassie Brilliant Blue 0.05% (w/v) in 10% (v/v) acetic acid for a minimum of 16 hrs to allow complete and uniform staining. The stained gel was then destained in 10% (v/v) acetic acid until the background contained no visible residual dye. The gel was then scanned on a laser densitometer (LKB, Ultrascan XL Laser Densitometer). Representative portions of the gel without protein were randomly chosen and scanned to determine background absorption for an accurate baseline. The region to be scanned for each lane containing PA was then visually aligned to insure that the entire protein peak and adequate baseline were included in each scan. The scans were completed and the integration values were determined using the LKB preprogrammed Gaussian algorithm and later were confirmed by cutting out individual peaks and manually integrating based on peak weight. The resulting integration values were plotted using Sigmaplot (Jandel). Linear regression of the results revealed typical r values of 0.992–0.996. The linear standard curve was then used to quantitate the amount of 83 kDa PA in the various fermentation samples based on the same integration methods.

Purification: The exact volume and conductivity of the PA in DEA buffer was determined and solid KCl was added to the solution to a final concentration of 30 mM and conductivity of 10–11 mmhos/cm. The PA was pumped with a peristaltic pump through a monoQ column prepared by collecting 100 mls of hydrated Bio-Rad Macro Prep 50Q on a sintered glass filter and washing sequentially with 1 liter of 25 mM DEA, 50 mM NaCl, 1 mM EDTA, 50 μM OP and 0.1 mM PMSF pH8.9 and 1 liter of the same buffer with 30 mM KCl added. The conductivity (10–11 mmhos/cm) and pH of 8.9 of the eluate from the Macro Prep 50Q after the second wash were comparable to that of the PA solution after addition of KCl. The Macro Prep 50Q resin was then degassed and slurry packed into a Pharmacia K column with a Rainin Rabbit-Plus peristaltic pump at 48 rpm and a flow rate of 15 mls/min. The final column volume was (5×5 cm) 98 mls. The PA solution was pumped through the Macro Prep 50Q column at a rate of 10 mls/min and the eluate was collected until all of the PA sample volume was loaded and the column washed with an additional 100 mls of DEA/KCl buffer. The eluate containing unbound PA was concentrated and diafiltered using an 1-ft$^2$ 30 kDa cutoff cellulosic Amicon wound spiral cartridge at an operating pressure of 20 psi.

The final concentrate (ca. 400 mls, 6–7 mmhos/cm) was passed through a 0.2$\mu$ cellulose acetate filter. The filtered PA was loaded onto a Poros IIQ perfusion chromatography column using a quaternary Waters 600E HPLC pump. The column was prepared by hydrating seven grams of the Poros IIQ perfusion resin in twice the packed bed volume of 2% (w/v) NaCl. After settling the resin was resuspended in six times the packed bed volume of 25 mM DEA pH 8.9, 50 mM NaCl, 7.5% (v/v) ethylene glycol and allowed to settle overnight at room temperature. The resin was then resuspended in three times the packed bed volume and finally in one and one-half times the final volume before the slurry was extensively degassed using a vacuum pump (vacuum unknown). The entire degassed slurry was then transferred to a Waters AP 20×100 mm glass HPLC column and the column was packed in one step using the Waters 600E pumps at a flow rate of 20 mls/min and a backpressure of 650 psi at room temperature. The column separation efficiency was then tested at a flow rate of 10 mls/min using a linear 1 M NaCl gradient and ovalbumin 5 mg/ml (Sigma) and bovine serum albumin 10 mg/ml (Sigma) in DEA as buffer as standard proteins. Approximately 100 mls of PA (ca. 20–30 mg PA) cooled to 4–6° C. was applied to the column and followed with a 20 min wash in the starting buffer at room temperature to elute unbound material. The column was then developed with a linear gradient to 30% of the 1 M NaCl DEA elution buffer. The purified PA was found to elute between 10–15%, while the smaller molecular weight proteolytic breakdown products eluted as a shoulder or partially resolved peak at 16–20% of the elution buffer. The resolution of the two peaks was found to be a function of content of PA proteolytic degradation products. The eluant was monitored at 280 nm and peak fractions were collected by manual triggering of an ISCO fraction collector. Samples of the peak fractions were diluted into 5–10 volumes of TRIS pH8.0, 0.1 mM PMSF, 50 AM OP, 1 mM EDTA buffer and concentrated using Amicon Centricon 30 concentrators at 4500×g at 4° C. to approximately the initial sample volume. An equal volume of SDS-PAGE solubilization buffer was added to the sample immediately prior to heating at 95° C. for 5 min. Purity was assessed from 8–25% SDS-PAGE PHAST gels (Pharmacia) and fractions with the highest purity were combined and dialyzed against 40–50 volumes of 25 mM DEA pH8.9, 50 mM NaCl, 0.1 mM PMSF and 2 mM EDTA at 4° C. for at least 16 hrs. Fractions judged empirically to be less than 95% pure were rechromatographed under the same conditions and purity of the fractions was reassessed as described above. All fractions of greater than 95% purity were ultimately combined, aliquoted and frozen at −70° C. subsequent to determination of the total PA concentration.

Analysis and characterization of purified 83 kDa PA: Purified PA was quantitated by measuring UV-absorption at 280 nm using the relationship of 1 $A_{280nm}$ in a 1 cm pathlength cuvette is equals 1 mg PA/ml (Leppla, 1988). Results obtained in this manner were confirmed using the Bio-Rad Bradford protein assay under conditions suggested by the manufacturer. PA purity was assessed using SDS-PAGE under conditions described above. Capillary electrophoresis analytical assays have also proven promising in the assessment of PA purity and amounts of residual protease inhibitors in final product. Feasibility studies using a 47 cm×50 pm uncoated silica capillary and borate/SDS/acetonitrile buffer revealed an excellent separation of the protein from residual protease inhibitors. Quantitation of both protein and inhibitors has also proven possible, but the technique remains limited by the relatively high limits of detection (1 mM EDTA, 0.1 mM PMSF, and 0.05 mM OP) under current conditions. Automated N-terminal sequencing was carried out with purified PA using an Applied Biosystems 470A sequenator after desalting over Bio-Rad PD10 columns equilibrated with 5 mM NaCl and 1 mM $CaCl_2$. A unique N-terminal sequence was found and the first six residues of the sequence were identical to PA from the endogenous plasmid pXO1 harbored by the USAMRIID *B. anthracis* Sterne strain. In addition, the sequence corresponded exactly with the published DNA derived protein sequence (Welkos et al.). Native gel electrophoresis under non-denaturing conditions revealed that PA purified from ΔSterne-1(pPA102)CR4 also exhibited the microheterogeneity noted previously for PA produced by the Sterne strain. Cytotoxicity assays of the product using the macrophage lysis assay (Friedlander et al.) revealed that the titration curve of biological activity for PA from ΔSterne-1(pPA102) CR4 was indistinguishable from that generated for PA from the Sterne strain.

Evaluation of ΔSterne-1(pPA102)CR4:

EXAMPLE 1

*B. Anthracis* ΔSterne-1(pPA102)CR4 was compared with its parent spore-forming strain *B. anthracis* ΔSterne-1 (pPA102). Both organisms were plated onto sheep blood agar (a preferred medium for promoting bacterial spore production) and grown at 37° C. for 1 day, after which the temperature was lowered to 25° C. for 4 days. The two strains were also grown in liquid Leighton-Doi medium, which is designed to promote spore production, for 1 day at 37° C. followed by 4 days growth at 25° C. Growth from both agar and broth cultures were examined under phase contrast microscopy for the presence of spores. Growth from all four cultures were then resuspended in phosphate buffered saline to a concentration of about $10^9$ colony-forming units (CFU) per ml. All four cultures were then heat shocked at 64° C. for 60 minutes to kill vegetative cells. Aliquots of 0.1 ml of the heat shocked material was then plated out onto sheep blood agar and incubated at 37° C. for 2 days.

Results:

*B. anthracis* ΔSterne-1(pPA102): Spores were seen under microscopic examination of material from both the sheep blood agar cultures and the Leighton-Doi medium cultures. On sheep blood agar plates containing heat shocked culture material from both sheep blood agar cultures and Leighton-Doi medium cultures, there was confluent growth. The data clearly indicate that *B. anthracis* ΔSterne-1(pPA102) forms spores.

*B. anthracis* ΔSterne-1(pPA102) CR4: No spores were seen under microscopic examination of material from both the sheep blood agar cultures and the Leighton-Doi medium cultures. On sheep blood agar plates containing heat shocked cultures, there was no growth whatsoever. The data clearly indicate the *B. anthracis* ΔSterne-1(PPA102) CR4, which has been deposited in the American Type Culture Collection and has been assigned ATCC designation 69714, does not form spores. The deposit at the American Type Culture Collection located at 12301 Parklawn Drive, Rockville, Md. 20852, USA was made on Nov. 16, 1994.

EXAMPLE 2

*B. anthracis* ΔSterne-1(pPA102)CR4 was grown in an FA medium fermentor culture. No spores were seen upon phase contract microscopic examination. Only medium-length and long chains of bacilli were seen. Dilution plate counts on the culture determined that the culture contained $1.86 \times 10^9$ CFU per ml. Three ml of culture was heat shocked at 60° C. for 60 minutes, then 0.2 ml was plated onto each of 5 plates of Tryptic soy agar. After incubation for 2 days at 37° C., no colonies were seen on the agar plates, indicating that spore production in the fermentor was less than 1 per $1.86 \times 10^9$ CFU. On two other fermentation runs with this strain, similar results were obtained. No revertants to the parent spore-forming phenotype were observed.

The above process using an FA medium fermentor culture was repeated using the parent strain *B. anthracis* ΔSterne-1(pPA102). Growth on the tryptic soy agar after heat shock resulted in a total of 1000 total colonies, indicating that the parent strain *B. anthracis* ΔSterne-1(pPA102) had about 1000 spores per ml in the FA medium, or 1 spore per 106 CFU in the non-heat shocked medium.

EXAMPLE 3

Protective antigen (PA) was prepared in accord with the teachings under Materials and Methods as described above. The purified PA of *B. anthracis* ΔStern-1(pPA102)CR4 was mixed in different buffers (phosphate buffered saline, HEPES, Tris, glycyl glycine (GG), sodium citrate, for example) and combined with monophosphoryl lipid A (MPL), Squalene, Tween 80 and lecithin. The mixture was then lyophilized. At 0 and 4 weeks, vials of lyophilized MPL/PA/emulsion were reconstituted in phosphate buffered saline (PBS) and injected in 0.5 ml doses containing 50 μg of PA per dose. At 10 weeks, the guinea pigs were aerosol challenged with approximately 36 medial lethal doses of virulent *Bacillus anthracis* spores of the Ames strain. The following data shows status two weeks after the challenge.

| Vaccine | S/T* | % | Anti-PA** |
|---|---|---|---|
| PA in PBS (+ MPL emulsion) | 10/12 | 83 | 29,427 |
| PA in GG (+ MPL emulsion) | 14/16 | 88 | 23,713 |
| PA in Tris (+ MPL emulsion) | 15/16 | 94 | 27,384 |
| PA in HEPES (+ MPL emulsion) | 15/15 | 100 | 25,482 |
| PA in Citrate (+ MPL emulsion) | 16/16 | 100 | 31,622 |
| PBS | 0/4 | 0 | <10 |

*Survived/Total, day 14 post-challenge
**Prechallenge serum titers to PA were determined by enzyme linked immunosorbent assay. The geometric mean reciprocal titers were calculated for each group and are expressed in this table.

What is claimed is:

1. A method of making a vaccine comprising: incorporating a protective antigen produced by recombinant asporogenic *B. anthracis* with a pharmaceutically acceptable carrier, wherein said recombinant asporogenic *B. anthracis* was isolated from a ΔSterne-1(pPA102) strain of bacteria and said recombinant asporogenic *B. anthracis* does not have the ability to bind a dye when grown on Congo Red Agar.

2. The method of claim 1, wherein the recombinant asporogenic *B. anthracis* is *B. Anthracis* ΔSterne-1(pPA 102)CR4.

3. The method of claim 1, wherein the vaccine is in the form of a suspension.

4. The method of claim 1 wherein the vaccine is in the form of buffered suspension.

5. The method of claim 1 wherein said carrier is an adjuvant.

* * * * *